United States Patent
Billard et al.

(10) Patent No.: US 12,239,352 B2
(45) Date of Patent: Mar. 4, 2025

(54) REMOVABLE SPLIT CANNULA FOR PLACEMENT OF ELECTRODES

(71) Applicant: Zimmer Biomet CMF and Thoracic, LLC, Jacksonville, FL (US)

(72) Inventors: Max Holland Billard, Jacksonville, FL (US); Perry Twyford, Jacksonville, FL (US)

(73) Assignee: Zimmer Biomet CMF and Thoracic, LLC, Jacksonville, FL (US)

( * ) Notice: Subject to any disclaimer, the term of this patent is extended or adjusted under 35 U.S.C. 154(b) by 371 days.

(21) Appl. No.: 17/668,091

(22) Filed: Feb. 9, 2022

(65) Prior Publication Data

US 2022/0265335 A1      Aug. 25, 2022

Related U.S. Application Data (60) Provisional application No. 63/147,367, filed on Feb. 9, 2021.

(51) Int. Cl.
*A61B 17/90* (2006.01)
*A61B 17/00* (2006.01)

(52) U.S. Cl.
CPC ........ *A61B 17/90* (2021.08); *A61B 17/00234* (2013.01); *A61B 2017/00292* (2013.01)

(58) Field of Classification Search
CPC .............. A61B 17/90; A61B 17/00234; A61B 2017/00292; A61B 17/3417; A61B 90/50;
(Continued)

(56) References Cited

U.S. PATENT DOCUMENTS

| 4,865,593 A | 9/1989 | Ogawa et al. |
| 5,318,542 A | 6/1994 | Hirsch et al. |

(Continued)

FOREIGN PATENT DOCUMENTS

| DE | 3347150 | 7/1985 |
| DE | 102015218958 | 12/2016 |

(Continued)

OTHER PUBLICATIONS

"Application Serial No. PCT US2022 015802, Invitation to Pay Additional Fees mailed May 30, 2022", 12 pgs.
(Continued)

*Primary Examiner* — Shaun L David
*Assistant Examiner* — Rachael L Geiger
(74) *Attorney, Agent, or Firm* — SCHWEGMAN LUNDBERG & WOESSNER, P.A.

(57) ABSTRACT

A method of inserting an electrode into a cranial cavity of a cranium can include determining a length, between a target within the cranial cavity and a proximal end of a multipiece cannula, of the electrode for insertion of the electrode to the target. A distal end of the electrode can be inserted through a multipiece cannula supported by an instrument holder of a surgical arm. The surgical arm can be positioned such that a distance from the target to the proximal end of the cannula is equal to the length. The electrode can be fed through the cannula and through the anchor bolt into the cranial cavity. Feeding of the electrode through the cannula and into the cranial cavity can be stopped when the length of the electrode fed into the cavity reaches the length between the proximal opening of the multipiece cannula and the target.

15 Claims, 7 Drawing Sheets

(58) Field of Classification Search
CPC . A61B 17/3468; A61B 17/3421; A61B 34/32; A61B 90/03; A61B 90/11; A61B 90/14; A61B 2017/347; A61B 2034/102; A61B 2090/034; A61B 2090/103; A61B 34/30; A61N 1/0534; A61N 1/0539

See application file for complete search history.

(56) References Cited

U.S. PATENT DOCUMENTS

| | | | |
|---|---|---|---|
| 6,027,480 | A | 2/2000 | Davis et al. |
| 6,080,141 | A | 6/2000 | Castro et al. |
| 7,033,326 | B1* | 4/2006 | Pianca ............... A61N 1/0534 600/585 |
| 7,879,024 | B2 | 2/2011 | Thorstenson et al. |
| 8,755,906 | B2 | 6/2014 | Moffitt et al. |
| 10,695,492 | B2 | 6/2020 | Mccullough et al. |
| 10,716,834 | B2 | 7/2020 | Bratbak et al. |
| 2004/0002629 | A1 | 1/2004 | Branch et al. |
| 2004/0098020 | A1 | 5/2004 | Nardeo |
| 2005/0197663 | A1 | 9/2005 | Soma et al. |
| 2011/0224681 | A1 | 9/2011 | Mcdonald |
| 2014/0200550 | A1 | 7/2014 | Farnan et al. |
| 2015/0224282 | A1 | 8/2015 | Christiansen |
| 2017/0007349 | A1 | 1/2017 | Solar et al. |
| 2019/0099597 | A1* | 4/2019 | Mirro ............... A61N 1/0534 |

FOREIGN PATENT DOCUMENTS

| | | |
|---|---|---|
| EP | 2907539 | 8/2015 |
| JP | 2012508594 A | 4/2012 |
| JP | 2014054541 A | 3/2014 |
| JP | 2020096829 A | 6/2020 |
| JP | 2024509366 | 3/2024 |
| WO | 2022173817 | 8/2022 |

OTHER PUBLICATIONS

"International Application Serial No. PCT US2022 015802, International Search Report mailed Jul. 21, 2022", 7 pgs.

"International Application Serial No. PCT US2022 015802, Written Opinion mailed Jul. 21, 2022", 9 pgs.

"International Application Serial No. PCT US2022 015802, International Preliminary Report on Patentability mailed Aug. 24, 2023", 11 pgs.

"Australian Application Serial No. 2022218700, First Examination Report mailed Jun. 14, 2024", 3 pgs.

"Australian Application Serial No. 2022218700, Response filed Sep. 26, 2024 to First Examination Report mailed Jun. 14, 2024", 15 pgs.

"European Appliation Serial No. 22707938.1, Response Filed Mar. 26, 2024 to Communication pursuant to Rules 161(1) and 162 EPC mailed Sep. 19, 2023", 16 pgs.

"Japanese Application Serial No. 2023-547788, Notification of Reasons for Refusal mailed Jul. 16, 2024", w/ English translation, 13 pgs.

* cited by examiner

REMOVABLE SPLIT CANNULA FOR PLACEMENT OF ELECTRODES

CLAIM OF PRIORITY

This application claims the benefit of U.S. Provisional Patent Application Ser. No. 63/147,367, filed on Feb. 9, 2021, the benefit of priority of which is claimed hereby, and which is incorporated by reference herein in its entirety.

BACKGROUND

Neurosurgical operations are common in modern medicine to help patients with a variety of conditions. Some conditions can be effectively treated using minimally invasive surgical procedures where very small incisions and access bores are used to access a patient's cranial cavity. Such minimally invasive procedures require small tools, such as needles and electrodes, and precisely obtained measurements.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Some neurosurgical minimally invasive procedures require precise placement of a probe or needle through a cranium of a patient and to a target within the patient's cranium, typically a portion of a brain or a tumor. In some cases, an electrode is placed through a bore in the cranium to a target. The electrode can be relatively long and flexible and can be guided to its target by an anchor bolt secured to the patient's cranium where the anchor bolt can guide a trajectory of the electrode to the target.

A depth of insertion of the electrode to the target can be determined by calculating a distance from the target to a landmark outside the patient, such as a location on their skull. However, once insertion of the electrode begins it can be difficult to know how much more electrode must be inserted. So, a surgeon or physician can mark the electrode, accommodating for the skull, the anchor bolt, a cap, and any other items between a distal end of the electrode and a proximal end of the electrode that will still be visible once the target is reached. Such a measurement can require various steps and can take a considerable amount of time during an electrode placement procedure.

The inventors have recognized that the above process can be simplified and performed more precisely or accurately when a robotic surgical arm is used. Following registration of the patient and the surgical arm, a control system can use imaging data to determine a distance required to reach the target from a proximal end of a cannula. The electrode can be marked at this length and the surgical arm can be positioned a location where the electrode will be inserted to the target when the mark reaches the distal end of the cannula. This process can save time in measuring and marking and can increase accuracy and precision in placing the electrode.

One issue with this method is that the cannula required to guide the electrode is too small for a proximal connector of the electrode to pass through the cannula. The inventors have recognized that a cannula including a removable portion and a remainder portion can be used to help solve this problem. Once the electrode is placed at the target and the electrode is secured in its position at the target, the cannula can be disassembled to allow the proximal connector of the electrode to pass through the cannula, helping to increase accuracy and precision in placing the electrode and helping to save time during the procedure.

The above discussion is intended to provide an overview of subject matter of the present patent application. It is not intended to provide an exclusive or exhaustive explanation of the invention. The description below is included to provide further information about the present patent application.

Figure 1:
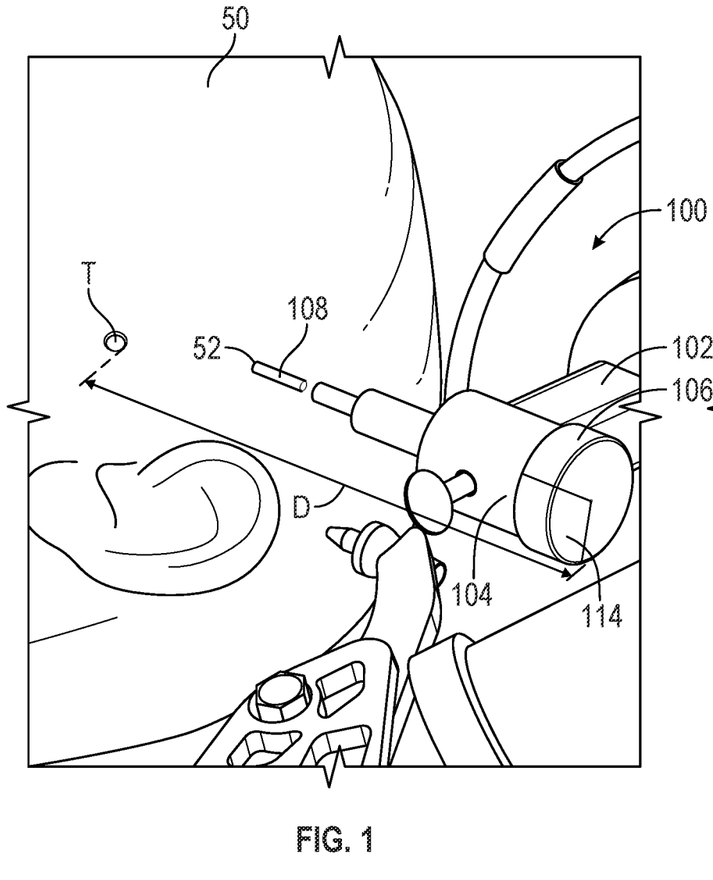
FIG. 1 illustrates a perspective view of a surgical system and a cranium.
Figure 2:
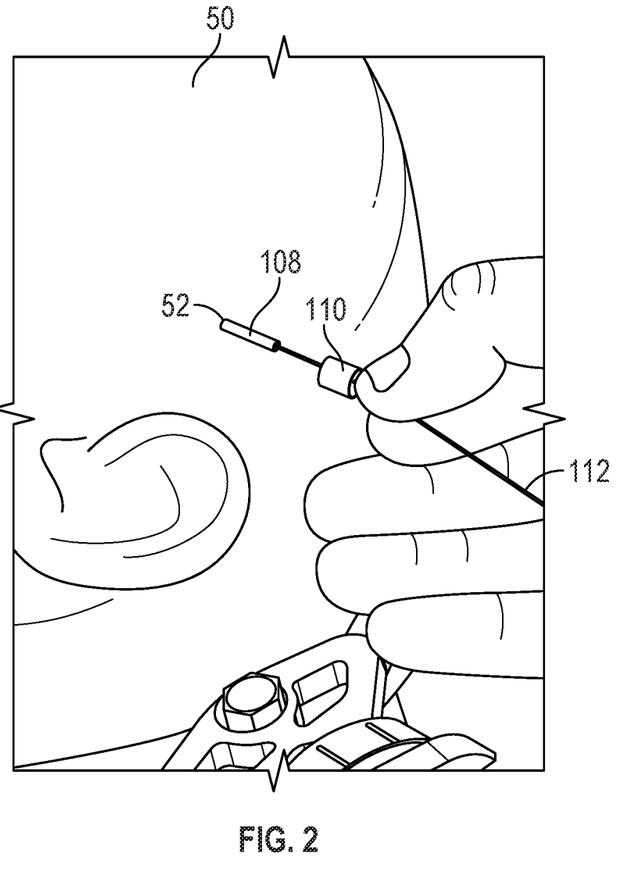
FIG. 2 illustrates a perspective view of a surgical system and a cranium.

FIG. 1 illustrates a perspective view of a surgical system 100 and a cranium 50. FIG. 2 illustrates a perspective view of the surgical system 100 and the cranium 50. FIGS. 1 and 2 are discussed together below. The cranium can include a bore or a bone tunnel 52. The surgical system 100 can include a surgical arm 102 and an end effector 103 (including a tool holder 104), a cannula 106, and an anchor bolt 108. FIG. 2 shows that the surgical system can include a cap 110 and an electrode 112. FIG. 1 also shows a target T.

During a neurosurgery procedure, the bone tunnel 52 or bore can be created in the cranium 50 for access to a cranial cavity of the patient, such as for access to the patient's brain or a tumor therein. Once the bore 52 is created, the bone anchor 108 can be secured to the bore 52. The bone anchor 108 can be secured at an angle to guide an electrode (or other instrument) at a proper trajectory to reach the target within the cranial cavity. The cap 110 can be secured to the bone anchor 108 to help capture and guide the electrode.

The surgical arm 102 can be an arm connected to a controller (as discussed in further detail below) and can be operated to move within space. The surgical arm 102 can be registered to landmarks of the patient (e.g., skull) so that the surgical arm 102 (or controller thereof) knows the position of the surgical arm 102 with respect to the cranium 50 and bore 52. The control system of the surgical arm 102 can use imaging data to determine a distance D required to reach the target from a proximal end 114 of the cannula 106. The electrode 112 can be marked at this length or distance and the surgical arm 102 can be positioned to a location where the electrode 112 will be inserted at the target T when the mark reaches the proximal end 114 of the cannula 106. This process can save time in measuring and marking and can increase accuracy and precision and accuracy in placing the electrode.

Figure 3:
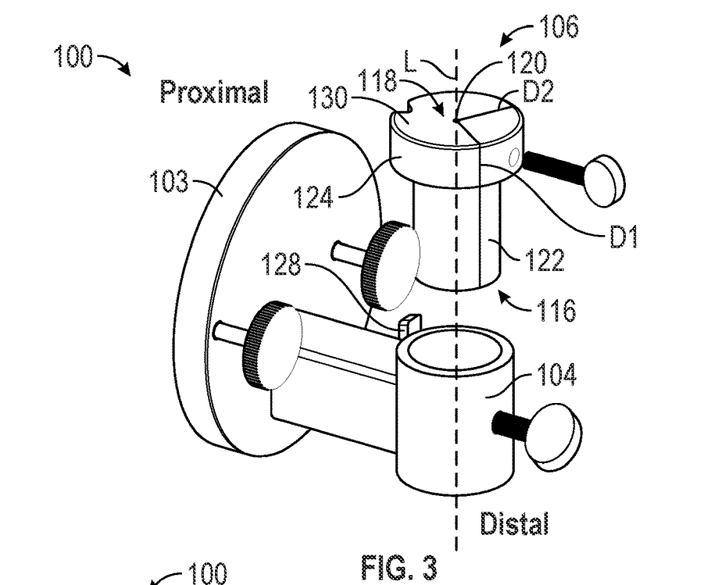
FIG. 3 illustrates a perspective view of a portion of a surgical system.
Figure 4:
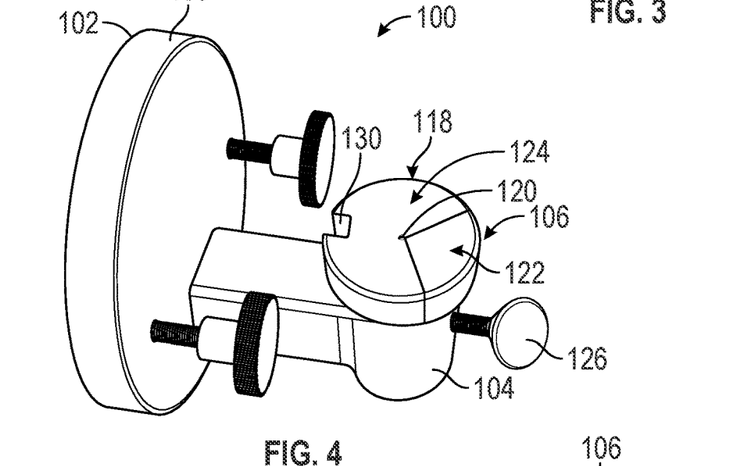
FIG. 4 illustrates a perspective view of a portion of a surgical system.
Figure 5:
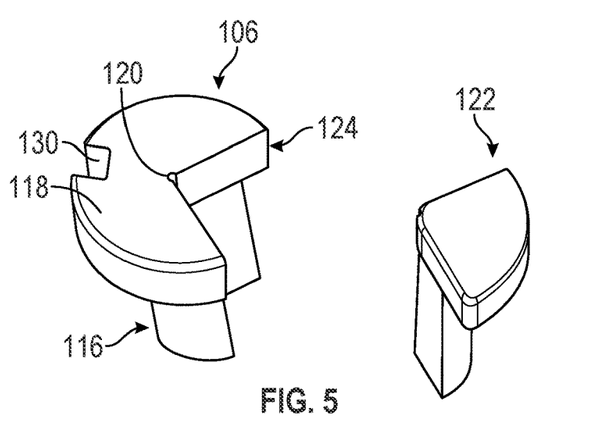
FIG. 5 illustrates a perspective view of a portion of a surgical system.

One issue with this method is that the cannula required to guide the electrode is too small for a distal connector of the electrode to pass through the cannula. FIGS. 3-5 discuss a solution to this issue.

FIG. 3 illustrates a perspective view of a portion of the surgical system 100. FIG. 4 illustrates a perspective view of a portion of the surgical system 100. FIG. 5 illustrates a perspective view of a portion of the surgical system 100. FIGS. 3-5 shows that the cannula 106 can be made of multiple pieces and are discussed together below.

The cannula 106 can be a rigid or semi-rigid body comprised of materials such as one or more of metals, plastics, foams, elastomers, ceramics, composites, combinations thereof, or the like. As shown in FIG. 3, the cannula 106 can include a body 116 and a collar 118, which can together define a bore 120 extending along a longitudinal axis of the body 116. The body 116 and the collar 118 can together define a first portion 122 (or a separable portion or a removable portion) and a second portion 124 (or a remainder portion) where the first portion 122 can be separable from the second portion 124 along the planes P1 and P2. The planes P1 and P2 can be orthogonal to each other and orthogonal to the longitudinal axis L, such that the first portion 122 forms a wedge of 90 degrees of the cannula 106 from a proximal perspective.

In other examples, the planes P1 and P2, which can define cuts separating the first portion 122 and second portion 124, can be in other locations. For examples, the first portion 122 (or separable portion) can be defined by plains P1 and P2 that are between 5 degrees and 180 degrees apart.

When the first portion 122 and the second portion 124 are positioned together, as shown in FIG. 3, the cannula 106 can be insertable into the tool holder 104, as shown in FIG. 4. The cannula 106 can be inserted into the tool holder 104 such that the body 116 of the cannula is insertable into the tool holder 104 until the collar 118 contacts the tool holder to limit distal movement of the body 116 into the tool holder 104. Once positioned in the tool holder 104, the cannula 106 can be secured to the tool holder 104 using a set screw 126. Other fasteners can be used to secure the cannula 106 to the tool holder 104.

Also, when the cannula 106 is positioned within the tool holder 104, a post 128 of the tool holder can be inserted into a notch 130 of the collar 118 of the cannula 106. Engagement between the post 128 and the notch 130 can help to limit rotation of the cannula 106 with respect to the tool holder 104. The notch 130 can be oriented with respect to the separable portion 122 to position the separable portion 122 near the set screw 126, which can allow the set screw 126 to engage the separable portion 122 to force the separable portion up against the remainder portion 124. Such a force can help to hold the separable portion 122 and the reminder portion 124 together within the tool holder 104 during use of the cannula 106.

When it is desired to remove the cannula from the tool holder 104 (or to remove the first portion 122), the set screw 126 can be loosened and either the first portion 122 or the second portion 124 can be removed from the tool holder 104. As shown in FIG. 5, when the first portion 122 is separated from the second portion 124, the bore 120 is open to one side of the cannula 106, such that the bore 120 is radially incomplete when the first portion 122 is separated from the second portion 124. Such separation can allow for an electrode or other small instrument within the bore 120 to be moved out of the bore 120 radially. Then, a larger portion of the electrode (or instrument), such as a connector, can pass through the larger opening of the cannula 106 created by removal of the first portion 122.

Alternatively, when the first portion 122 is separated from the second portion 124, the first portion 122 can be removed from the tool holder 104. Then, because the instrument within the bore 120 is no longer captured by the cannula 106, the second portion 124 can also be removed from the cannula, allowing any larger part of the instrument (e.g., electrode) to be passed through the tool holder 104.

Figure 6:
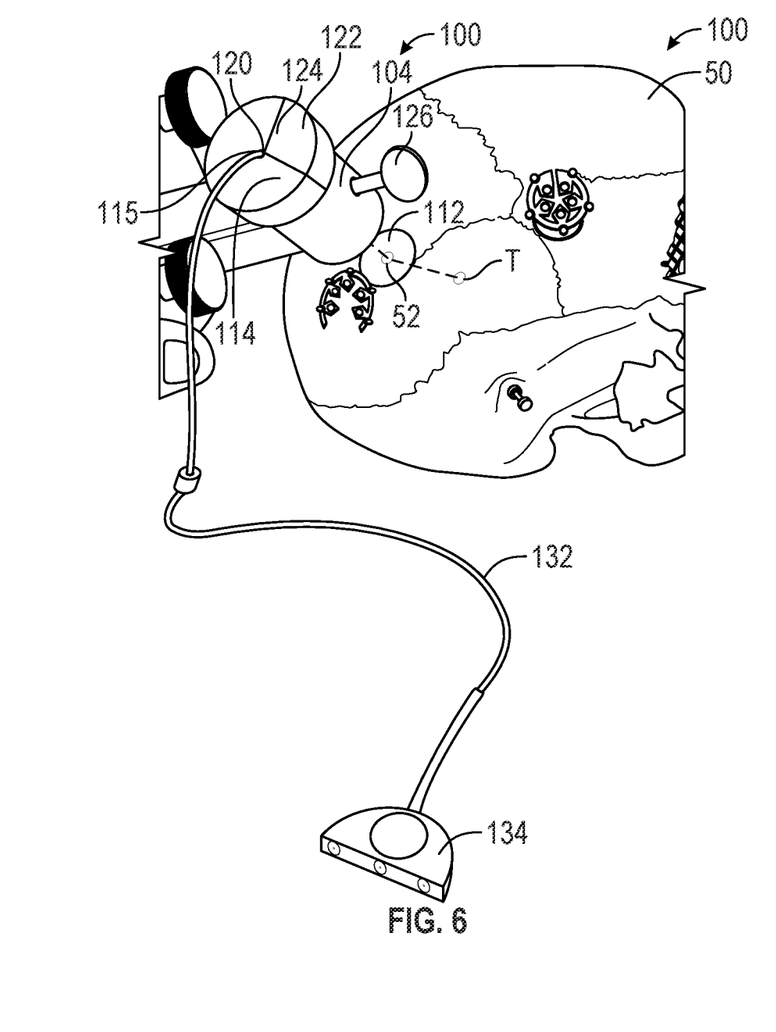
FIG. 6 illustrates a perspective view of a portion of a surgical system and a cranium.
Figure 7:
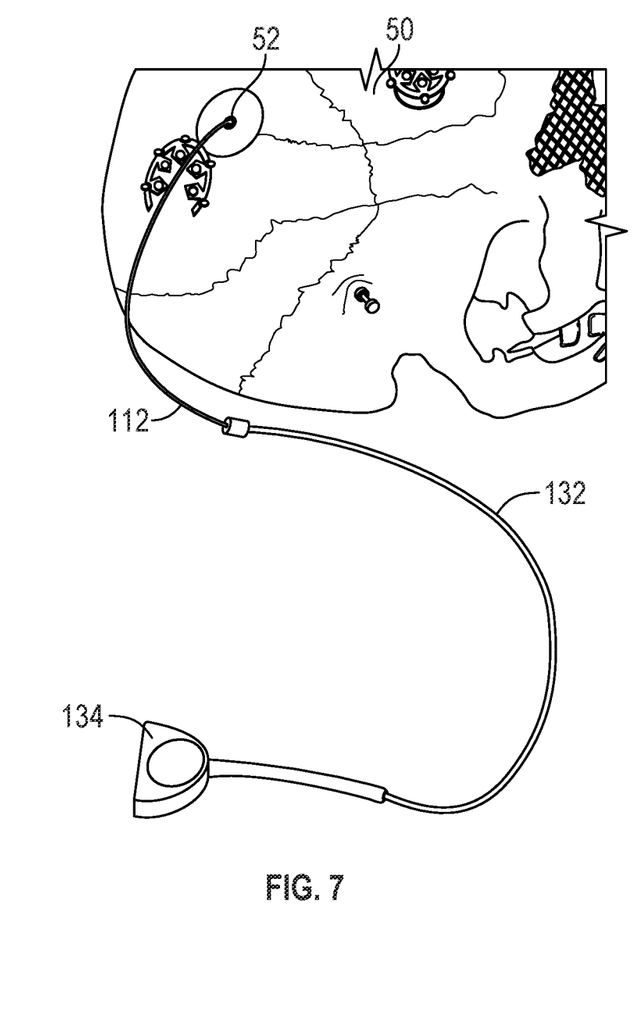
FIG. 7 illustrates a perspective view of a portion of a surgical system and a cranium.

FIG. 6 illustrates a perspective view of a portion of the surgical system 100 and the cranium 50. FIG. 7 illustrates a perspective view of a portion of the surgical system and the cranium 50. FIGS. 6 and 7 are discussed together below.

After marking of the electrode, as discussed above with respect to FIGS. 1 and 2, the electrode can be fed through the bore 120 of the cannula 106 and through the anchor 108 and the bore 52 and to the target T until a distal end 113 of the electrode 112 reaches the target as indicated by a mark 115 on the electrode reaching the proximal end 114 of the cannula 106. At this point, the surgeon can stop feeding the electrode 112 and the cap 110 can be tightened onto the anchor bolt 108 to secure the electrode 112 to the anchor bolt 108 and therefore to secure the electrode 112 with respect to the cranium 50 and the target T.

Once the electrode 112 is secured, the set screw 126 can be unscrewed from the tool holder 104 and the first portion 122 of the cannula 106 can be separated and removed from the remainder portion 124 and from the tool holder 104. Optionally, the remainder portion 124 can be removed from the tool holder 104. Removal of one or more of the first portion 122 and the second portion 124 can provide clearance to allow for a lead 132 and connector 134 of the electrode 112 to pass through the tool holder 104.

Figure 8:
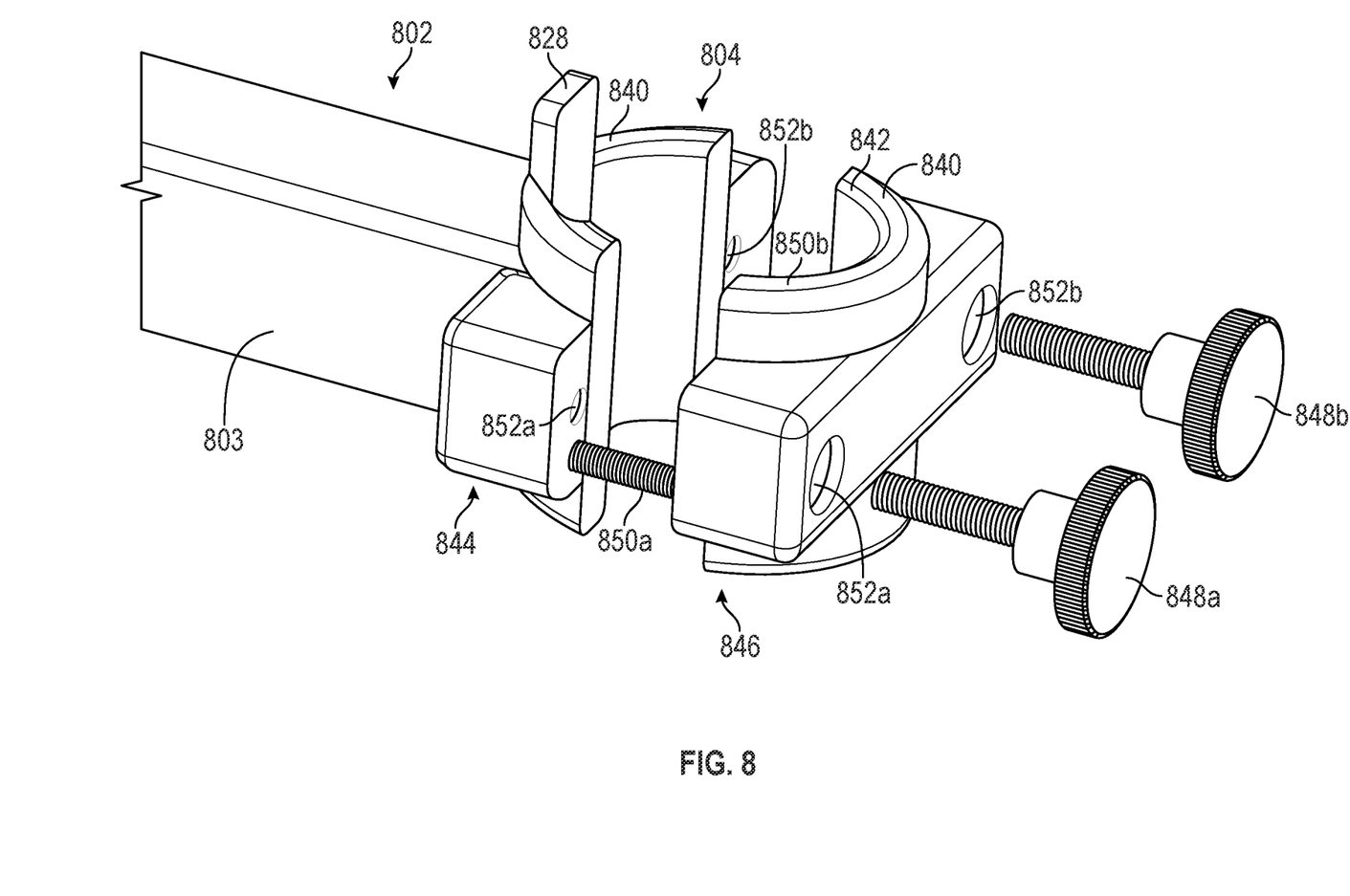
FIG. 8 illustrates a perspective view of a portion of a surgical system.

FIG. 8 illustrates a perspective view of a portion of a surgical system 800. The surgical system 800 can be similar to the surgical system 100; the surgical system 800 can differ in that the system 800 can include an instrument holder 804 with two separable portions. The surgical system 100 can be modified to include such an instrument holder.

The instrument holder 804 can include a post 828 and a collar 840 defining a bore 842. The instrument holder 804 can also include a first portion 844, a second portion 846, bolts 848a and 848b, and guide rods 850a and 850b. The second portion 846 can include bores 852a and 852b.

The instrument holder 804 can connect to a surgical arm, such as via an end effector 803 or end effector coupler. The first portion 844 can be connected to the second portion 846 via guide rods 850a and 850b, which can move into bores of the first portion 844 or the second portion 846. When the first portion 844 and the second portion 846 are abutted, the first portion 844 and the second portion 846 can form a complete collar 840 to define the bore 842 for retaining a cannula (such as the cannula 106). The bolts 848a and 848b can be threadable into the bores 852a and 852b to secure the first portion 844 to the second portion 846. Similarly, the first portion 844 and the second portion 846 can be separated by unthreading the bolts 848 from the bores 852 and pulling the first portion 844 and the second portion 846 apart.

During operation, such as when implanting an electrode, a connector of the electrode, such as the connector 134, may not ben able to pass through a bore of the cannula or even through the bore 842 of the instrument holder following removal of the cannula (such as the multipiece cannula 106).

In such a case, the bolts 84*a* can be loosened or removed from the bores 852 and the first portion 844 and the second portion 846 of the tool holder 804 can be separated to increase the size of the bore 842 or to remove the second portion 846 from the end effector 803 entirely, to free the connector. Such a tool holder can allow for the method described above (of positioning the end of the cannula to denote when the electrode has reached its target) to be used even where the electrode has a very large proximal connector.

Figure 9:
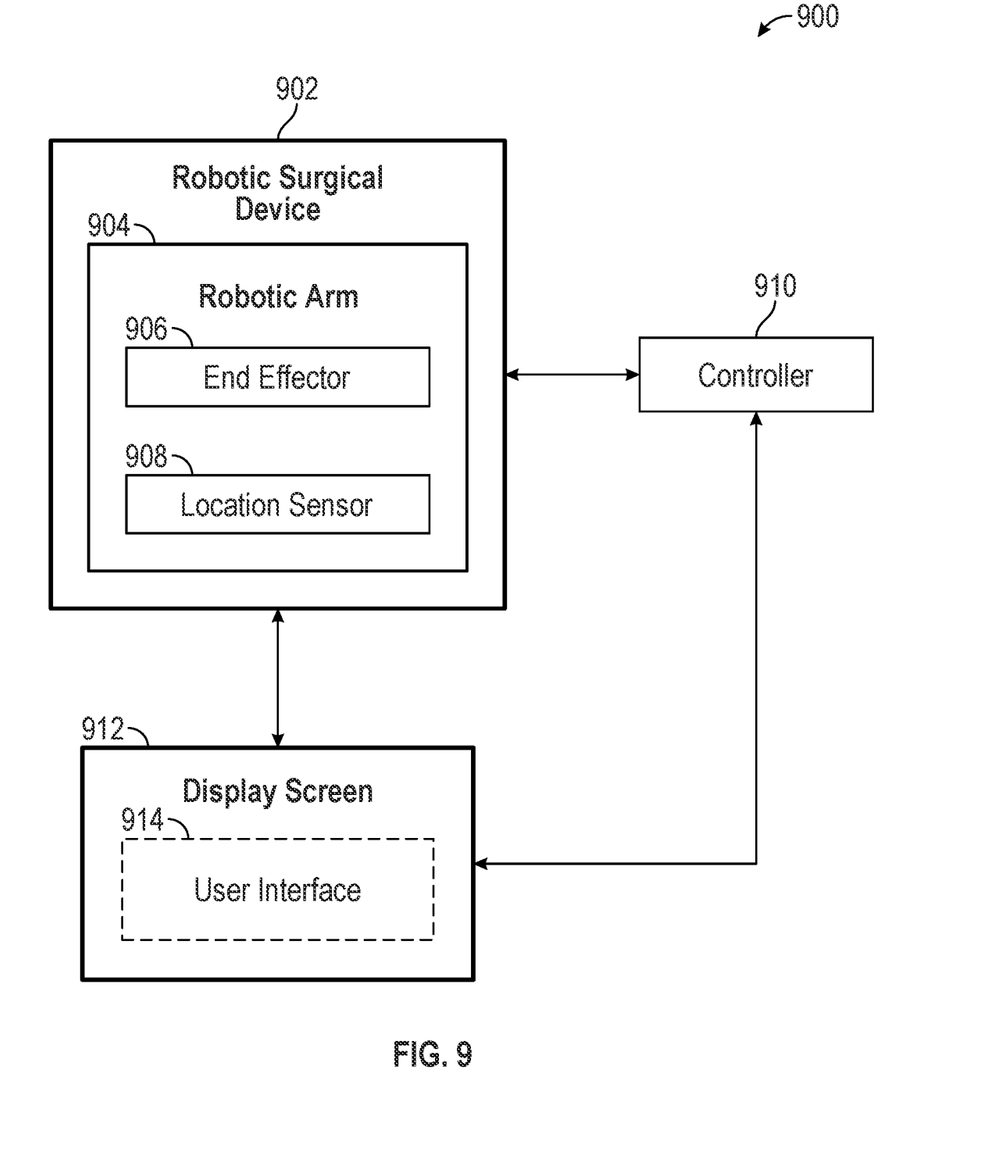
FIG. 9 illustrates a schematic of a surgical system.

FIG. 9 illustrates a schematic of a surgical system 900 for robotically assisted insertion of an electrode or surgical instrument, in accordance with at least one example of the present application. The robotic surgical system 900 can include a robotic surgical device 902, which can include a robotic arm 904 including an end effector 906 and a location sensor 908. The system 900 can be a part of the system 100 discussed above.

The controller 910 can be a programmable controller, such as a single or multi-board computer, a direct digital controller (DDC), a programmable logic controller (PLC), or the like. In other examples the controller 910 can be any computing device, such as a handheld computer, for example, a smart phone, a tablet, a laptop, a desktop computer, or any other computing device including a processor, memory, and communication capabilities.

The location sensor 908 can be one or more proximity sensors connected to the robotic arm 904 and in communication with the controller 910. The location sensor can be configured to transmit a signal to the controller based on a location of the arm (such as a location of the end effector 906 or position of the end effector 906) with respect to the space or other landmarks.

The display 912 can be a monitor, display, or any other device configured to display data or images received from the controller 910 or the robotic surgical device. The user interface 914 can be any display and/or input device. For example, user interface can be a monitor, keyboard, and mouse in one example. In other examples, the user interface 914 can be a touch screen display. In yet another example, the user interface 914 can provide lights, buttons, and/or switches. The controller 910 and the user interface 914 can include machine readable medium. The terms "machine readable medium" may include any medium that is capable of storing, encoding, or carrying instructions for execution by the device and that cause the device to perform any one or more of the techniques of the present disclosure, or that is capable of storing, encoding or carrying data structures used by or associated with such instructions. Non-limiting machine readable medium examples may include solid-state memories, and optical and magnetic media. Specific examples of machine readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The robotic arm 904 can be controlled by a surgeon with various control devices or systems. For example, a surgeon can use the user interface 914 (e.g., via the controller 910 that is processor-implemented based on machine-readable instructions, which when implemented cause the robotic arm to move automatically or to provide force assistance to surgeon-guided movement) to guide the robotic arm 904. The controller 910 can include a computing system, which can communicate with the display screen 912. A surgeon can use anatomical imaging displayed on the display screen 912 to guide and position the robotic arm 904. Anatomical imaging can be provided to the display screen 912 from various imaging sources, such as one or more cameras positioned on the end effector 906, or from a C-arm providing preoperative or intraoperative fluoroscopy.

The controller 910 can receive pre-operative, intra-operative, or post-operative medical images. These images can be received in any manner and the images can include, but are not limited to, computed tomography (CT) scans, magnetic resonance imaging (MRI), two-dimensional x-rays, three-dimensional x-rays, ultrasound, or the like. These images in one example can be sent via a server as files attached to an email. In another example, the images can be stored on an external memory device such as a memory stick and coupled to a USB port of the robotic system to be uploaded into the processing unit. In yet other examples, the images can be accessed over a network by the control system 910 from a remote storage device or service.

In some examples, after receiving one or more images, the controller 910 can generate one or more virtual models related to a surgical area. Alternatively, the controller 910 can receive virtual models of the anatomy of the patient prepared remotely. Specifically, a virtual model of the anatomy of a patient can be created by defining anatomical points within the image(s) and/or by fitting a statistical anatomical model to the image data. The virtual model, along with virtual representations of the surgical system (e.g., arm and cannula), can be used for calculation. In one procedure type, the virtual model can be utilized to determine insertion location, trajectory and depth for inserting an instrument, such as an instrument received or integrated into the end effector 906. In a specific example, the virtual model can be used to determine a depth of insertion for an electrode.

The robotic arm 904 can move autonomously in an example. In another example, the robotic arm 904 can provide a force assist or a force resistance to surgeon or user guided movements. In yet another example, a combination of autonomous movement and force assistance or force resistance movement can be performed by the robotic arm 904 (e.g., force assistance or force resistance for an initial movement, and autonomously moving a later movement). In an example, the robotic arm 904 can resist an applied force. For example, the robotic arm 904 can be programmed to stay within a particular range of locations or a particular position, move at a particular speed (e.g., resist a higher speed by resisting force), or the like.

The robotic surgical device 902 can output or receive data from the controller 910. In one example, the controller 910 can output information to a display screen 912. The display screen 912 can retrieve and display information from an imaging camera. The sensor 908 can be or can include an imaging camera that can be an optical navigation camera physically positioned on the robotic surgical device 902, such as on the robotic arm 904 or the end effector 906. The imaging camera can also be a C-arm or O-arm, to capture intraoperative fluoroscopic images. In an example, the display screen 912 can be used to display the user interface 914. A user can interact with the display screen 912 and the user interface 914 to input control commands, which can be relayed to the robotic surgical device 902 through the controller 910 to control the robotic surgical device 902. The robotic surgical system 900 can be used to perform all, or a portion of, a surgical procedure on a patient.

In the operation of some examples, a user can interact with the user interface 914 on the display screen 912 to power on the robotic surgical device 902. Power can be indicated by a light, for example, on the user interface 914, or on the robotic arm 902. When the robotic surgical device 902 is powered on, the user can operate the robotic arm 904 to operate the end effector 906 and any tools therein. A registration process can be performed thereafter, where location markers are secured to the patient and the robotic arm and sensors, such as the location sensor 908 or optical tracking devices, are configured to detect the location of the patient and the robotic arm and to allow the system 900 to update the location of the arm 904 and the patient throughout a surgical procedure.

Figure 10:
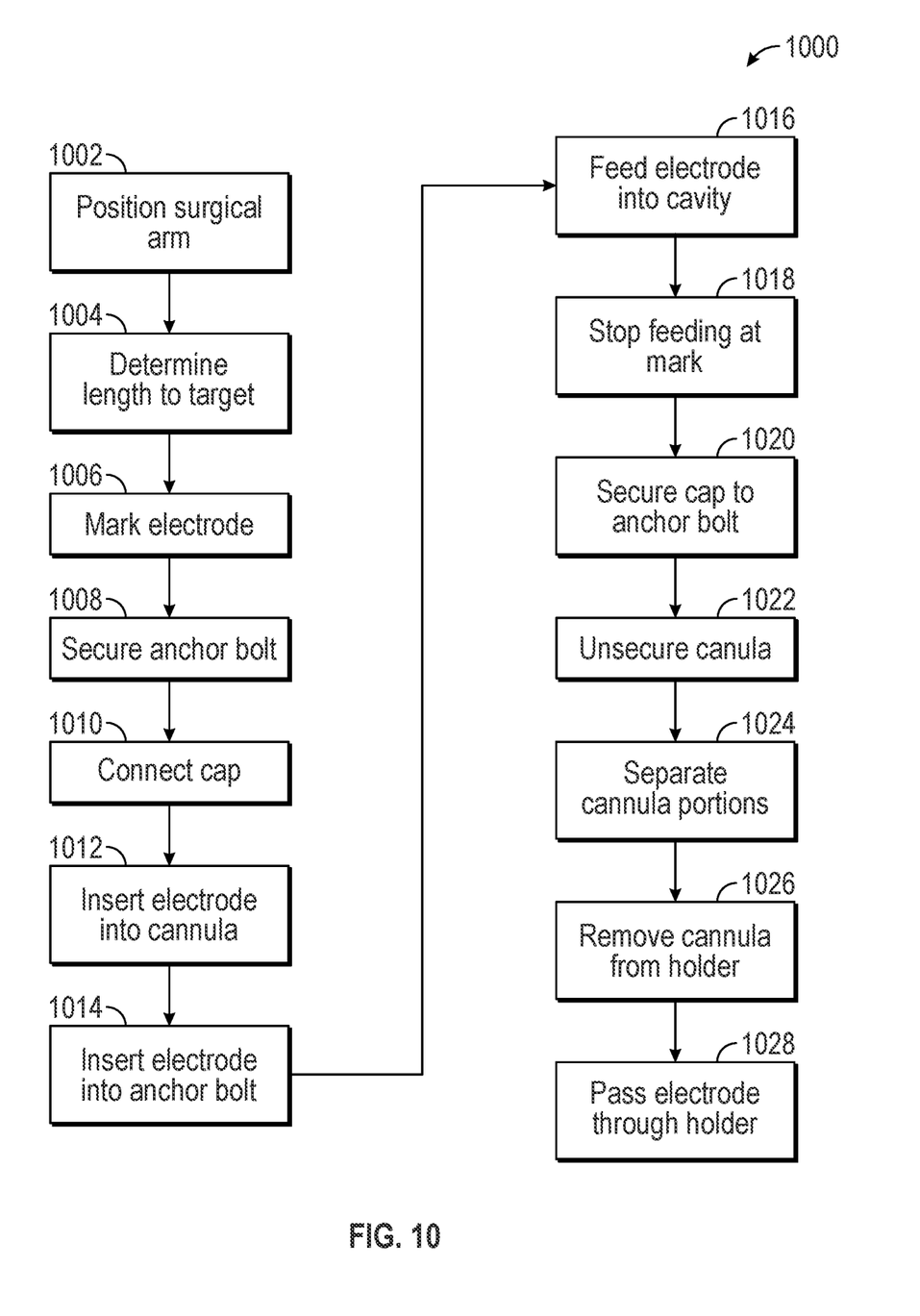
FIG. 10 illustrates a flow schematic of a method of operating a surgical system.

In some examples, the robotic surgical system 900 (e.g., the controller 910) can receive imaging or other data regarding a patient, such as scans of a patient's cranium. The controller 910 can also receive a target location within the cranium. In some examples, the user interface 914 can be used to set a target location. Once the target location is determined, either by the user or by the system 900, the surgical procedure can continue at step 1002, discussed below. Though the method 1000 discussed below does not explicitly include the steps discussed with respect to FIG. 9, these steps, among others, can be included in the method 1000.

FIG. 10 illustrates a schematic view of the method 1000, in accordance with at least one example of this disclosure. The method 1000 can be a method of guiding an electrode to a target using a surgical arm and a multipiece cannula. More specific examples of the method 1000 are discussed below. The steps or operations of the method 1000 are illustrated in a particular order for convenience and clarity; many of the discussed operations can be performed in a different sequence or in parallel without materially impacting other operations. The method 1000 as discussed includes operations performed by multiple different actors, devices, and/or systems. It is understood that subsets of the operations discussed in the method 1000 can be attributable to a single actor, device, or system could be considered a separate standalone process or method.

At step 1002, the surgical arm can be positioned. For example, the surgical arms 102 or 904 can be positioned by the controller near the skull or cranium 50. At step 1004, a length of the electrode for insertion at a target within the cranial cavity can be determined. For example, the distance D (of FIG. 1) can be determined by the controller 910, such as based on imaging and target selection (as discussed above with respect to FIG. 9) and based on known dimensions of the tool holder 104 and the cannula 106 and a position of the surgical arm. At step 1006, the electrode can be marked at the determined length.

At step 1006, an anchor bolt can be secured to the cranium at a location 9 and angle to guide the electrode to the target. For example, the anchor bolt 108 can be secured to the cranium 50. Then, at step 1010 a cap can be connected to the anchor bolt, such as the cap 110 and the anchor bolt 108 of FIG. 2. At step 1012, a distal end of the electrode can be inserted through a multipiece cannula supported by an instrument holder of a surgical arm. For example, a distal end of the electrode 112 can be inserted through the bore 120 of the cannula 106. At step 1014, a distal end of the electrode can be inserted into the cap and the anchor bolt, such as the cap 110 and the anchor bolt 108.

At step 1016, the electrode can be fed through the cannula and through the anchor bolt into the cranial cavity towards the target. For example, the electrode 112 can be fed through the cap 110 and the anchor bolt 108 and into the cranium 50. At step 1018, feeding of the electrode through the cannula and into the cranial cavity can be stopped when the mark of the electrode reaches a proximal opening of the multipiece cannula. For example, feeding of the electrode 112 can be stopped when the mark 115 reaches the proximal end 114 of the cannula 106 (as shown in FIG. 6).

At step 1020, the cap can be secured to the anchor bolt to fix position of the electrode relative to the anchor bold and to the cranium. For example, the cap 110 can be secured to the anchor bolt 108 to fix the position of the electrode 112. At step 1022, the cannula can be unscrewed from the surgical arm. For example, the set screw 126 can be unscrewed from the tool holder 104 and disengaged from the cannula 106. At step 1024, a separable portion of the cannula can be separated or removed from a remainder of the cannula and from the instrument holder. For example, the separable portion 122 can be separated from the remainder portion 124 and can be removed from the tool holder 104. Optionally, the remainder portion of the cannula can be removed from the instrument holder (e.g., the reminder portion 124 can be removed from the instrument holder 104). At step 1026, a proximal end of the electrode (such as a connector) can be passed through the cannula and the instrument holder. For example, the connector 134 can be passed through the tool holder 104 and optionally through the cannula 106. Such a process allows the surgical arm to be used determine and indicate a depth of the electrode to be installed, which can save time during a procedure by reducing a number of measurements and calculations performed during the procedure and while helping to increase accuracy and precision of the placement of the electrode.

Figure 11:
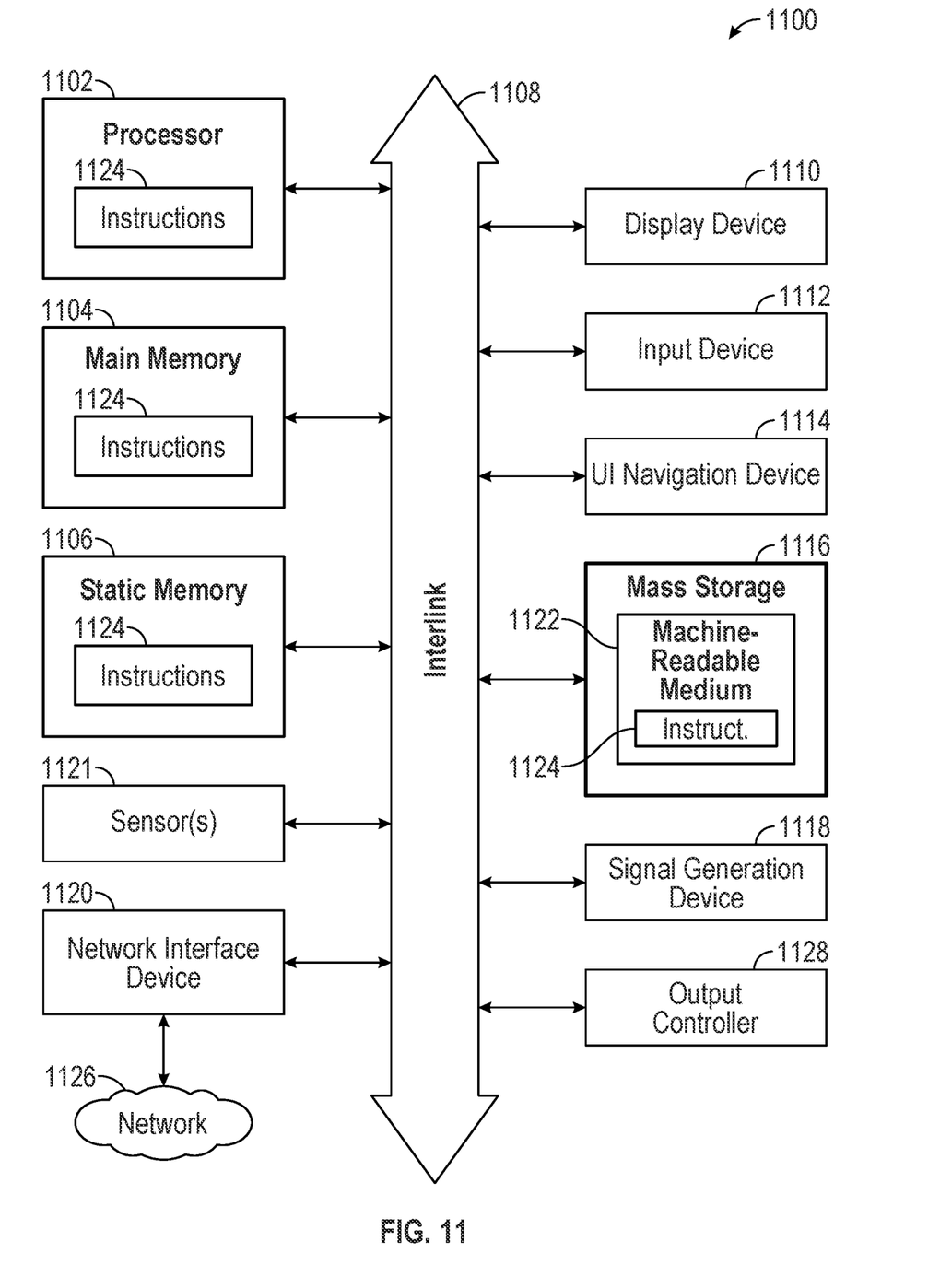
FIG. 11 is a block diagram illustrating an example of a machine upon which one or more embodiments may be implemented.

FIG. 11 illustrates a block diagram of an example machine 1100 upon which any one or more of the techniques (e.g., methodologies) discussed herein may perform. Examples, as described herein, may include, or may operate by, logic or a number of components, or mechanisms in the machine 1100. Circuitry (e.g., processing circuitry) is a collection of circuits implemented in tangible entities of the machine 1100 that include hardware (e.g., simple circuits, gates, logic, etc.). Circuitry membership may be flexible over time. Circuitries include members that may, alone or in combination, perform specified operations when operating. In an example, hardware of the circuitry may be immutably designed to carry out a specific operation (e.g., hardwired).

In an example, the hardware of the circuitry may include variably connected physical components (e.g., execution units, transistors, simple circuits, etc.) including a machine readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuitry in hardware via the variable connections to carry out portions of the specific operation when in operation. Accordingly, in an example, the machine readable medium elements are part of the circuitry or are communicatively coupled to the other components of the circuitry when the device is operating. In an example, any of the physical components may be used in more than one member of more than one circuitry. For example, under operation, execution units may be used in a first circuit of a first circuitry at one point in time and reused by a second circuit in the first circuitry, or by a third circuit in a second circuitry at a different time. Additional examples of these components with respect to the machine 1100 follow.

In alternative embodiments, the machine 1100 may operate as a standalone device or may be connected (e.g., networked) to other machines. In a networked deployment, the machine 1100 may operate in the capacity of a server machine, a client machine, or both in server-client network environments. In an example, the machine 1100 may act as a peer machine in peer-to-peer (P2P) (or other distributed) network environment. The machine 1100 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

The machine (e.g., computer system) 1100 may include a hardware processor 1102 (e.g., a central processing unit (CPU), a graphics processing unit (GPU), a hardware processor core, or any combination thereof), a main memory 1104, a static memory (e.g., memory or storage for firmware, microcode, a basic-input-output (BIOS), unified extensible firmware interface (UEFI), etc.) 1106, and mass storage 1108 (e.g., hard drive, tape drive, flash storage, or other block devices) some or all of which may communicate with each other via an interlink (e.g., bus) 1130. The machine 1100 may further include a display unit 1110, an alphanumeric input device 1112 (e.g., a keyboard), and a user interface (UI) navigation device 1114 (e.g., a mouse). In an example, the display unit 1110, input device 1112 and UI navigation device 1114 may be a touch screen display. The machine 1100 may additionally include a storage device (e.g., drive unit) 1108, a signal generation device 1118 (e.g., a speaker), a network interface device 1120, and one or more sensors 1116, such as a global positioning system (GPS) sensor, compass, accelerometer, or other sensor. The machine 1100 may include an output controller 1128, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

Registers of the processor 1102, the main memory 1104, the static memory 1106, or the mass storage 1108 may be, or include, a machine readable medium 1122 on which is stored one or more sets of data structures or instructions 1124 (e.g., software) embodying or utilized by any one or more of the techniques or functions described herein. The instructions 1124 may also reside, completely or at least partially, within any of registers of the processor 1102, the main memory 1104, the static memory 1106, or the mass storage 1108 during execution thereof by the machine 1100. In an example, one or any combination of the hardware processor 1102, the main memory 1104, the static memory 1106, or the mass storage 1108 may constitute the machine readable media 1122. While the machine readable medium 1122 is illustrated as a single medium, the term "machine readable medium" may include a single medium or multiple media (e.g., a centralized or distributed database, and/or associated caches and servers) configured to store the one or more instructions 1124.

The term "machine readable medium" may include any medium that is capable of storing, encoding, or carrying instructions for execution by the machine 1100 and that cause the machine 1100 to perform any one or more of the techniques of the present disclosure, or that is capable of storing, encoding or carrying data structures used by or associated with such instructions. Non-limiting machine readable medium examples may include solid-state memories, optical media, magnetic media, and signals (e.g., radio frequency signals, other photon based signals, sound signals, etc.). In an example, a non-transitory machine readable medium comprises a machine readable medium with a plurality of particles having invariant (e.g., rest) mass, and thus are compositions of matter. Accordingly, non-transitory machine-readable media are machine readable media that do not include transitory propagating signals. Specific examples of non-transitory machine readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 1124 can include any of the steps or processes discussed above and can be further transmitted or received over a communications network 1126 using a transmission medium via the network interface device 1120 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as Wi-Fi®, IEEE 802.16 family of standards known as WiMax®), IEEE 802.15.4 family of standards, peer-to-peer (P2P) networks, among others. In an example, the network interface device 1120 may include one or more physical jacks (e.g., Ethernet, coaxial, or phone jacks) or one or more antennas to connect to the communications network 1126. In an example, the network interface device 1120 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 1100, and includes digital or analog communications signals or other intangible medium to facilitate communication of such software. A transmission medium is a machine readable medium.

NOTES AND EXAMPLES

The following, non-limiting examples, detail certain aspects of the present subject matter to solve the challenges and provide the benefits discussed herein, among others.

Example 1 is a method of inserting an electrode into a cranial cavity of a cranium, the method comprising: determining a length, between a target within the cranial cavity and a proximal end of a multipiece cannula, of the electrode for insertion of the electrode to the target; inserting a distal end of the electrode through a multipiece cannula supported by an instrument holder of a surgical arm; positioning the surgical arm such that a distance from the target to the proximal end of the cannula is equal to the length; feeding the electrode through the cannula and through an anchor bolt into the cranial cavity; and stopping feeding of the electrode through the cannula and into the cranial cavity when the length of the electrode fed into the cavity reaches the length between the proximal end of the multipiece cannula and the target.

In Example 2, the subject matter of Example 1 optionally includes removing a separable portion of the cannula from the instrument holder; and passing a proximal end of the electrode through the cannula and the instrument holder.

In Example 3, the subject matter of Example 2 optionally includes removing a remaining portion of the cannula from the instrument holder.

In Example 4, the subject matter of Example 3 optionally includes increasing an opening size of the instrument holder.

In Example 5, the subject matter of any one or more of Examples 1-4 optionally include marking the electrode at the length; and stopping feeding of the electrode through the cannula and into the cranial cavity when the mark of the electrode reaches a proximal opening of the multipiece cannula.

In Example 6, the subject matter of any one or more of Examples 1-5 optionally include securing the anchor bolt to the cranium at a location and angle to guide the electrode to the target; and connecting a cap to the anchor bolt.

In Example 7, the subject matter of Example 6 optionally includes inserting the distal end of the electrode into a cap and the anchor bolt.

In Example 8, the subject matter of Example 7 optionally includes securing the cap to the anchor bolt to fix position of the electrode relative to the anchor bolt and to the cranium.

In Example 9, the subject matter of any one or more of Examples 1-8 optionally include unsecuring the cannula from the surgical arm.

Example 10 is a method of inserting an electrode into a cranial cavity of a cranium, the method comprising: determining a length, between a target within the cranial cavity and a proximal end of a multipiece cannula, of the electrode for insertion of the electrode to the target; inserting a distal end of the electrode through a multipiece cannula supported by an instrument holder of a surgical arm; positioning the surgical arm such that a distance from the target to the proximal end of the cannula is equal to the length; feeding the electrode through the cannula and through an anchor bolt into the cranial cavity; stopping feeding of the electrode through the cannula and into the cranial cavity when the length of the electrode fed into the cavity reaches the length between the proximal end of the multipiece cannula and the target; removing a separable portion of the cannula from the instrument holder; and passing a proximal end of the electrode through the cannula and the instrument holder.

In Example 11, the subject matter of Example 10 optionally includes removing a remaining portion of the cannula from the instrument holder.

In Example 12, the subject matter of Example 11 optionally includes increasing an opening size of the instrument holder.

In Example 13, the subject matter of any one or more of Examples 10-12 optionally include marking the electrode at the length; and stopping feeding of the electrode through the cannula and into the cranial cavity when the mark of the electrode reaches a proximal opening of the multipiece cannula.

In Example 14, the subject matter of any one or more of Examples 10-13 optionally include securing the anchor bolt to the cranium at a location and angle to guide the electrode to the target; and connecting a cap to the anchor bolt.

In Example 15, the subject matter of Example 14 optionally includes inserting the distal end of the electrode into the cap and the anchor bolt.

In Example 16, the subject matter of Example 15 optionally includes securing the cap to the anchor bolt to fix position of the electrode relative to the anchor bolt and to the cranium.

Example 17 is a cannula for guiding an electrode for insertion into a cranial cavity, the cannula comprising: a body defining a longitudinal axis and defining a bore extending through the body along the longitudinal axis; and a collar connected to and extending radially outward from a proximal portion of the body, the collar engageable with a surgical arm to orient the cannula with respect to the surgical arm, the body and the collar together defining a separable portion and a remainder portion, the separable portion separable from the remainder portion to expose the bore.

In Example 18, the subject matter of Example 17 optionally includes wherein the separable portion and the reminder portion are separable along longitudinal planes of the body.

In Example 19, the subject matter of Example 18 optionally includes wherein the longitudinal planes of the body are orthogonal to the longitudinal axis and orthogonal to each other.

Example 20 is a surgical system for guiding an electrode for insertion into a cranial cavity, the system comprising: a cannula comprising: a body defining a longitudinal axis and defining a bore extending through the body along the longitudinal axis; and a collar connected to and extending radially outward from a proximal portion of the body, the body and the collar together defining a separable portion and a remainder portion, the separable portion separable from the remainder portion to expose the bore; a robotic arm including an instrument holder configured to receive the cannula therein, the collar engageable with the instrument holder to orient the cannula with respect to the surgical arm; and a control system in communication with the robotic arm, the control system configured to operate the robotic arm to position the cannula.

In Example 21, the subject matter of Example 20 optionally includes wherein the control system is configured to receive a calculated distance from a proximal end of the cannula to a target within the cranial cavity.

In Example 22, the subject matter of Example 21 optionally includes wherein the control system is configured to position the cannula such that an actual distance between the proximal end of the cannula and the target is the calculated distance.

Example 23 is a cannula for guiding an electrode for insertion into a cranial cavity, the cannula comprising: a body defining a longitudinal axis and defining a bore extending through the body along the longitudinal axis; and a collar connected to and extending radially outward from a proximal portion of the body, the collar engageable with a surgical arm to orient the cannula with respect to the surgical arm, the body and the collar together defining a separable portion and a remainder portion, the separable portion separable from the remainder portion to expose the bore.

In Example 24, the subject matter of Example 23 optionally includes wherein the separable portion and the remainder portion are separable along longitudinal planes of the body.

In Example 25, the subject matter of Example 24 optionally includes wherein the longitudinal planes of the body are orthogonal to the longitudinal axis and orthogonal to each other.

In Example 26, the subject matter of any one or more of Examples 24-25 optionally include wherein the collar includes a notch engageable with a post of the surgical arm to limit rotation of the cannula with respect to the surgical arm.

In Example 27, the subject matter of any one or more of Examples 23-26 optionally include wherein the bore is configured to receive the electrode therethrough.

In Example 28, the subject matter of Example 27 optionally includes wherein the separable portion is separable from the remainder portion when the electrode is located within the bore.

In Example 29, the subject matter of any one or more of Examples 27-28 optionally include wherein the bore extends through at least a portion of the remainder portion and at least a portion of the separable portion.

Example 30 is a surgical system for guiding an electrode for insertion into a cranial cavity, the system comprising: a cannula comprising: a body defining a longitudinal axis and defining a bore extending through the body along the longitudinal axis; and a collar connected to and extending radially outward from a proximal portion of the body, the body and the collar together defining a separable portion and a remainder portion, the separable portion separable from the remainder portion to expose the bore; a robotic arm including an instrument holder configured to receive the cannula therein, the collar engageable with the instrument holder to orient the cannula with respect to the surgical arm; and a control system in communication with the robotic arm, the control system configured to operate the robotic arm to position the cannula.

In Example 31, the subject matter of Example 30 optionally includes wherein the control system is configured to receive a calculated distance from a proximal end of the cannula to a target within the cranial cavity.

In Example 32, the subject matter of Example 31 optionally includes wherein the control system is configured to position the cannula such that an actual distance between the proximal end of the cannula and the target is the calculated distance.

In Example 33, the subject matter of any one or more of Examples 30-32 optionally include wherein the separable portion and the remainder portion are separable along longitudinal planes of the body.

In Example 34, the subject matter of Example 33 optionally includes wherein the longitudinal planes of the body are orthogonal to the longitudinal axis and orthogonal to each other.

In Example 35, the subject matter of any one or more of Examples 31-34 optionally include wherein the collar includes a notch engageable with a post of the surgical arm to limit rotation of the cannula with respect to the surgical arm.

In Example 36, the subject matter of any one or more of Examples 30-35 optionally include wherein the bore is configured to receive the electrode therethrough.

In Example 37, the subject matter of Example 36 optionally includes wherein the separable portion is separable from the remainder portion when the electrode is located within the bore.

In Example 38, the subject matter of any one or more of Examples 36-37 optionally include wherein the bore extends through at least a portion of the remainder portion and at least a portion of the separable portion.

In Example 39, the apparatuses or method of any one or any combination of Examples 1-38 can optionally be configured such that all elements or options recited are available to use or select from.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The invention claimed is:

1. A method of inserting an electrode into a cranial cavity of a cranium, the method comprising:
determining a length, between a target within the cranial cavity and a proximal end of a multipiece cannula, of the electrode for insertion of the electrode to the target;
inserting a distal end of the electrode through the cannula supported by an instrument holder of a surgical arm;
positioning the surgical arm such that a distance from the target to the proximal end of the cannula is equal to the length;

feeding the electrode through the cannula and through an anchor bolt into the cranial cavity;
stopping feeding of the electrode through the cannula and into the cranial cavity when the length of the electrode fed into the cavity reaches the length between the proximal end of the multipiece cannula and the target;
removing a separable portion of the cannula from the instrument holder; and
passing a proximal end of the electrode through the cannula and the instrument holder, where the proximal end of the electrode includes a connector that is larger than a guide bore of the cannula.

2. The method of claim 1, further comprising:
removing a remaining portion of the cannula from the instrument holder.

3. The method of claim 2, further comprising:
increasing an opening size of the instrument holder.

4. The method of claim 1, further comprising:
marking the electrode at the length; and
stopping feeding of the electrode through the cannula and into the cranial cavity when the mark of the electrode reaches a proximal opening of the multipiece cannula.

5. The method of claim 1, further comprising:
securing the anchor bolt to the cranium at a location and angle to guide the electrode to the target; and
connecting a cap to the anchor bolt.

6. The method of claim 5, further comprising:
inserting the distal end of the electrode into a cap and the anchor bolt.

7. The method of claim 6, further comprising:
securing the cap to the anchor bolt to fix position of the electrode relative to the anchor bolt and to the cranium.

8. The method of claim 1, further comprising:
unsecuring the cannula from the surgical arm.

9. A method of inserting an electrode into a cranial cavity of a cranium,
the method comprising:
determining a length, between a target within the cranial cavity and a proximal end of a cannula made of multiple pieces, of the electrode for insertion of the electrode to the target;
inserting a distal end of the electrode through a cannula supported by an instrument holder of a surgical arm;
positioning the surgical arm such that a distance from the target to the proximal end of the cannula is equal to the length;
feeding the electrode through the cannula and through an anchor bolt into the cranial cavity;
stopping feeding of the electrode through the cannula and into the cranial cavity when the length of the electrode fed into the cavity reaches the length between the proximal end of the multipiece cannula and the target;
removing a separable portion of the cannula from the instrument holder; and
passing a proximal end of the electrode through the cannula and the instrument holder, where the proximal end of the electrode includes a connector that is larger than a guide bore of the cannula.

10. The method of claim 9, further comprising:
removing a remaining portion of the cannula from the instrument holder.

11. The method of claim 10, further comprising:
increasing an opening size of the instrument holder.

12. The method of claim 9, further comprising:
marking the electrode at the length; and
stopping feeding of the electrode through the cannula and into the cranial cavity when the mark of the electrode reaches a proximal opening of the multipiece cannula.

13. The method of claim 9, further comprising:
securing the anchor bolt to the cranium at a location and angle to guide the electrode to the target; and
connecting a cap to the anchor bolt.

14. The method of claim 13, further comprising:
inserting the distal end of the electrode into the cap and the anchor bolt.

15. The method of claim 14, further comprising:
securing the cap to the anchor bolt to fix position of the electrode relative to the anchor bolt and to the cranium.

* * * * *

UNITED STATES PATENT AND TRADEMARK OFFICE
CERTIFICATE OF CORRECTION

| | |
|---|---|
| PATENT NO. | : 12,239,352 B2 |
| APPLICATION NO. | : 17/668091 |
| DATED | : March 4, 2025 |
| INVENTOR(S) | : Billard et al. |

It is certified that error appears in the above-identified patent and that said Letters Patent is hereby corrected as shown below:

On the Title Page

On page 2, in Column 2, item (56) under "Other Publications", Line 13, delete "Appliation" and insert --Application-- therefor In the Claims In Column 14, Line 58, in Claim 1, after "cranium,", delete a linebreak In Column 15, Line 35, in Claim 9, after "cranium,", delete a linebreak Signed and Sealed this
Twenty-eighth Day of October, 2025

John A. Squires
*Director of the United States Patent and Trademark Office*